US009386927B2

(12) United States Patent
 Kaiser

(10) Patent No.: US 9,386,927 B2
(45) Date of Patent: Jul. 12, 2016

(54) IMPLANTABLE BLOOD PRESSURE MONITOR

(75) Inventor: Daniel R. Kaiser, Plymouth, MN (US)

(73) Assignee: Medtronic, Inc., Minneapolis, MN (US)

(*) Notice: Subject to any disclaimer, the term of this patent is extended or adjusted under 35 U.S.C. 154(b) by 1803 days.

(21) Appl. No.: 12/510,370

(22) Filed: Jul. 28, 2009

(65) Prior Publication Data

US 2011/0028851 A1 Feb. 3, 2011

(51) Int. Cl.
| A61B 5/08 | (2006.01) |
| A61B 5/0215 | (2006.01) |
| A61B 5/04 | (2006.01) |
| A61N 1/36 | (2006.01) |
| A61B 5/00 | (2006.01) |
| A61N 1/365 | (2006.01) |

(52) U.S. Cl.
CPC ............ *A61B 5/0215* (2013.01); *A61B 5/04001* (2013.01); *A61B 5/6846* (2013.01); *A61N 1/36114* (2013.01); *A61B 5/0031* (2013.01); *A61N 1/36564* (2013.01)

(58) Field of Classification Search
CPC ............... A61B 5/0215; A61B 5/6846; A61B 5/04001; A61B 5/0031; A61N 1/36114; A61N 1/36564
USPC .......................................... 600/481, 485, 486
See application file for complete search history.

(56) References Cited

U.S. PATENT DOCUMENTS

| 4,341,221 | A | 7/1982 | Testerman |
| 5,505,201 | A | 4/1996 | Grill, Jr. et al. |
| 5,919,220 | A | 7/1999 | Stieglitz et al. |
| 6,073,048 | A | 6/2000 | Kieval et al. |
| 6,093,197 | A | 7/2000 | Bakula et al. |
| 6,745,079 | B2 | 6/2004 | King |
| 7,486,991 | B2 | 2/2009 | Libbus et al. |
| 2006/0106429 | A1* | 5/2006 | Libbus et al. ................... 607/44 |
| 2007/0118038 | A1 | 5/2007 | Bodecker et al. |
| 2007/0156200 | A1 | 7/2007 | Kornet et al. |
| 2008/0161701 | A1* | 7/2008 | Bullens et al. ............... 600/481 |
| 2009/0062667 | A1 | 3/2009 | Fayram et al. |

OTHER PUBLICATIONS

Grassi, Guido; Cattaneo, Bianca; Seravalle, Gino; Lanfranchi, Antonio; and Mancia, Biuseppe. "Baroreflex Control of Sympathetic Nerve Activity in Essential and Secondary Hypertension". *Hypertension* 1998; vol. 31;68-72.
Kawada, Toru; Shishido, Toshiaki; Inagaki, Masashi et al. "Differential Dynamic Baroreflex Regulation of Cardiac and Renal Sympathetic Nerve Activities". *American Journal of Physiology—Heart and Circulatory Physiology* 2001;vol.280;H1581-H1590.

(Continued)

*Primary Examiner* — Patricia Mallari
*Assistant Examiner* — Tiffany Weston

(57) ABSTRACT

A method for monitoring blood pressure includes sensing and storing sympathetic nerve activity data of a patient via a recording lead of an implantable medical device. Changes in sympathetic nerve activity from the nerve activity data are determined. Corresponding changes in blood pressure are determined from the changes in sympathetic nerve activity. An alert signal and/or modification of therapy can be provided.

7 Claims, 5 Drawing Sheets

(56) References Cited

OTHER PUBLICATIONS

Potkay, Joseph A. "Long Term, Implantable Blood Pressure Monitoring Systems". *Biomed Microdevices* 2008;10:379-392.

Rea, Robert F. and Hamdan, Mohamed. "Baroreflex Control of Muscle Sympathetic Nerve Activity in Borderline Hypertension". *Circulation* 1990;82;856-862.

\* cited by examiner

IMPLANTABLE BLOOD PRESSURE MONITOR

Various implantable devices for measuring blood pressure are known. Some devices obtain direct measurement of arterial pressure using intravascular pressure transducers or other pressure sensors. Intra-arterial blood pressure devices may, however, increase thrombogenic risk, infection risk and require a complicated implantation procedure.

Other implantable devices are based on the principle of pulse transit time and may utilize sensors implanted adjacent to an artery or utilize direct cardiac methods of pressure measurement.

Various implantable devices for regulating blood pressure by stimulating cardiac afferent sympathetic nerves, carotid sinus nerves or other nerves of the sympathetic system are known. These devices either do not provide feedback pressure when applying therapy or use noninvasive measurements of pressure to represent the patient's physiological condition.

The present teachings provide an implantable blood pressure device and associated methods for chronic and indirect measurements of blood pressure by monitoring sympathetic nerve activity. Therapy may also be optionally administered.

SUMMARY

In various embodiments, the present teachings provide a method for monitoring blood pressure. The method includes sensing and storing sympathetic nerve activity data of a patient via a recording lead of an implantable medical device. Changes in sympathetic nerve activity from the nerve activity data are determined. Corresponding changes in blood pressure are determined from the changes in sympathetic nerve activity. An alert signal and/or modification of therapy can be provided.

In various embodiments, the method can include implanting a medical device including a processor and a storage module in a patient, coupling a first end of a recording lead to the medical device and inserting a second end of the recording lead adjacent a sympathetic nerve ending. The method also includes transmitting sympathetic nerve activity via the recording lead to the medical device and recording sympathetic nerve activity in the storage module as stored nerve activity data. Changes in sympathetic nerve activity can be determined from the stored nerve activity data. Corresponding changes in blood pressure can be determined from the changes in sympathetic nerve activity. An alert signal can be issued and/or therapy can be adjusted.

In various embodiments, the present teachings provide medical apparatus that includes a patient implantable medical device having a processor and a data storage module. The device can include a recording lead having a first end operably coupled to the implantable medical device and a second end operable for sensing and transmitting sympathetic nerve activity data when implanted adjacent to a nerve ending. The processor is operable to determine changes in blood pressure corresponding to changes in sympathetic nerve activity.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses.

The present teachings provide devices and methods for chronic indirect monitoring of blood pressure by monitoring and recording sympathetic nerve activity. The sympathetic nerve activity can be measured by using one or more electrodes positioned in close proximity to a nerve. The sympathetic nerve activity can be used to approximate changes in arterial blood pressure and central venous blood pressure, as described below.

Figure 1:
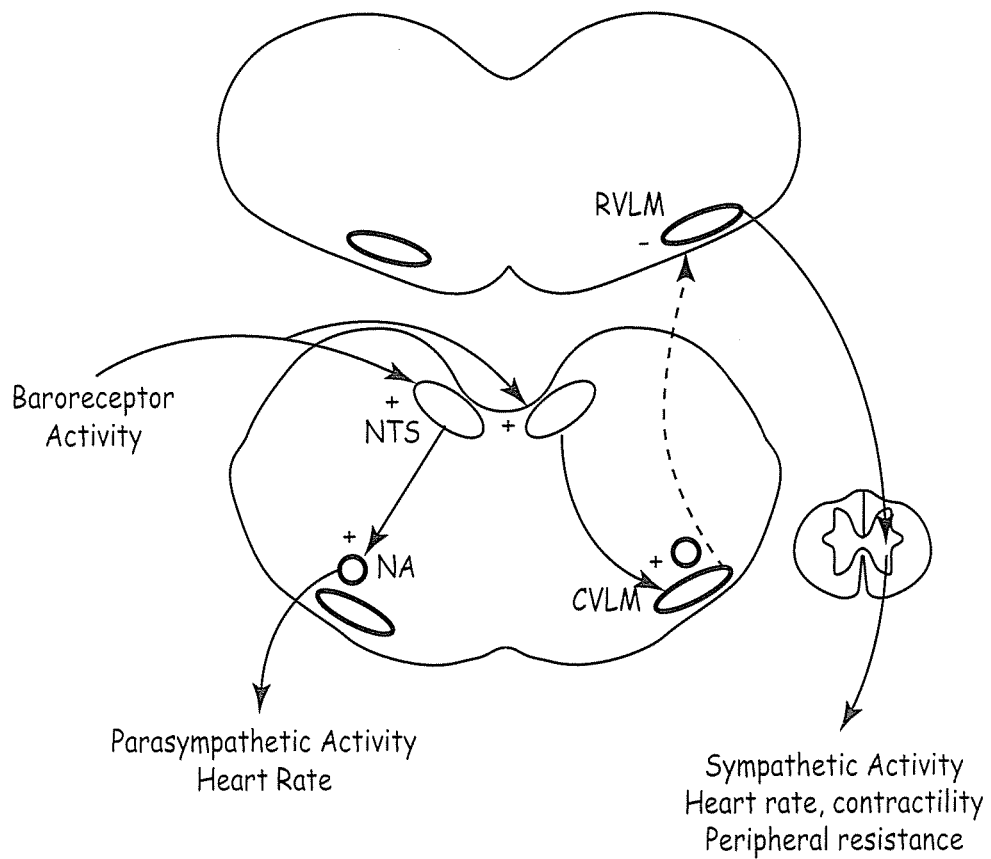
FIG. 1 is a schematic illustration of a biological feedback control system regulating arterial blood pressure.

Blood pressure is regulated through a feedback control system consisting of baroreceptors (biological pressure sensors) and effector mechanisms that modify resting levels of blood pressure within a range that ensures proper blood flow to end organs of the body. FIG. 1 illustrates schematically a negative feedback control system involved in regulating arterial blood pressure.

The baroreceptors are fine nerve endings that are activated by stretch of vessel walls located at the carotid sinuses and the aortic arch. The baroreceptors send afferent nerve activity as a function of stretch to the location of the brain known as the nucleus of the tractus solitarius (NTS). In turn, the NTS neurons activate neurons in the caudal ventrolateral medulla (CVLM), which inhibit neurons in the rostral ventrolateral medulla (RVLM), causing a reduction in the sympathetic preganglionic neuron activity in the spinal cord. Therefore, increasing blood pressure or stretch of the vessel walls results in a decrease in sympathetic activity. Similarly, a decrease in blood pressure causes an increase in sympathetic activity and activation of the RVLM.

Figure 2:
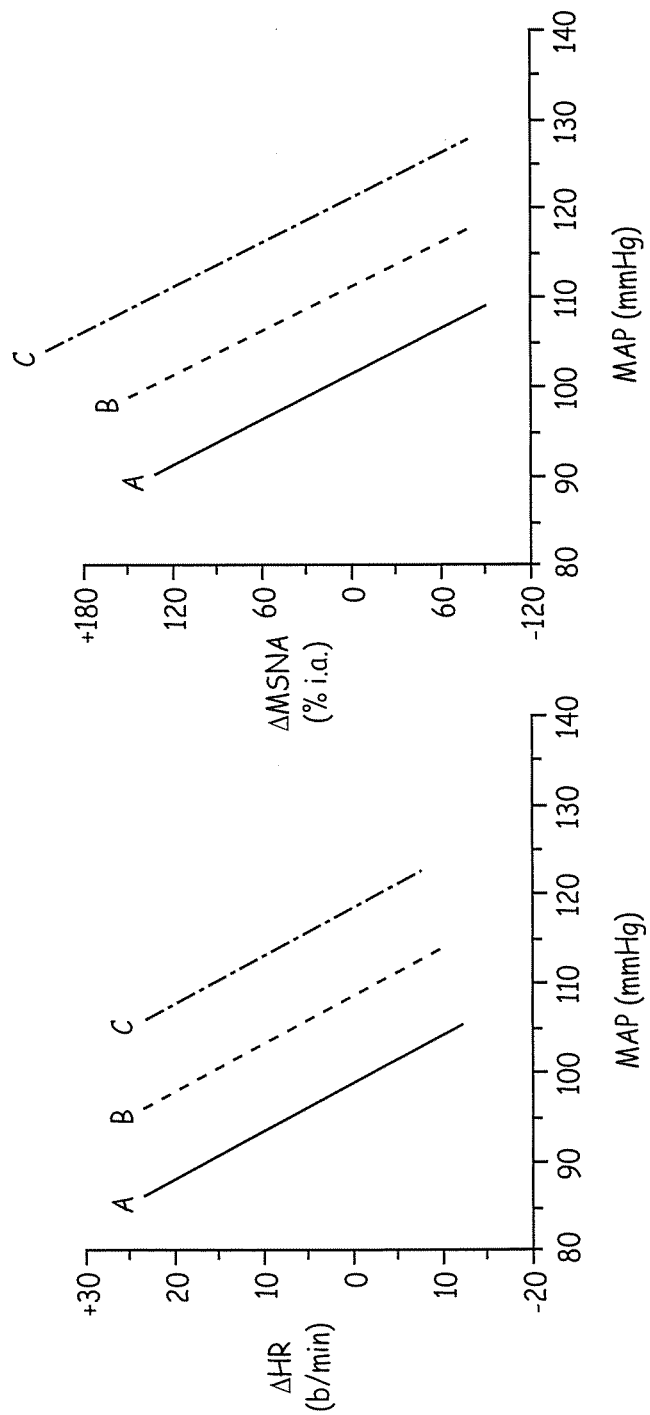
FIG. 2A is a graphic representation of the relation between changes in heart rate AHR and mean arterial pressure (MAP) in normotensive subjects (A) patients with moderate hypertension (B) and in patients with severe essential or secondary hypertension (C)
FIG. 2B is a graphic representation of the relation between changes in muscle sympathetic nerve activity AMNSA and mean arterial pressure (MAP) in normotensive subjects (A) patients with moderate hypertension (B) and in patients with severe essential or secondary hypertension (C)

In fact, there exists a linear relationship between the change in blood pressure and the change in sympathetic activity such that a measurement of sympathetic nervous system activity may be used to approximate changes in mean arterial blood pressure. FIG. 2A demonstrates the linear relationship between mean arterial pressure (MAP) and changes in heart rate (HR) over a physiologic range of pressure in different disease states. FIG. 2B demonstrates the linear relationship between MAP and changes in muscle sympathetic nerve activity (MSNA) over a physiologic range of pressure in different disease states. In FIGS. 2A and 2B, the relation on normotensive subjects (controls) is represented by line A; the relation in patients with moderate hypertension is represented by line B, and the relation in patients with more severe essential or secondary hypertension is represented by line C. The details of the studies and data obtained can be found in Grassi, G. et al., *Baroreflex Control of Sympathetic Nerve Activity in Essential and Secondary Hypertension*, Hypertension 1998; Vol. 31, pp 68-72, incorporated herein by reference.

As can be seen from FIGS. 1A and 2A, while the absolute arterial pressure is different when comparing normotensive and hypertensive patients, the slope of the relationship is nearly identical. For example, for a 180 percentage (%) drop in MSNA (i.a. units) there is a corresponding 20 mmHg increase in MAP. By measuring a median firing rate for sympathetic nerve activity, a baseline or threshold value "TV" can be established. Any increase or decrease in the firing rate, measured as a percentage, can be used to approximate a decrease, or increase, respectively, for mean arterial blood pressure.

Similarly, diastolic blood pressure may also be approximated using the percentage change in sympathetic nerve activity, as shown by Rea and Hamdan, *Baroreflex Control of Muscle Sympathetic Nerve Activity in Borderline Hypertension*, Circulation 1990, Vol. 82; pp 856-862. Additionally, it has been demonstrated that that the relationship between the measured change in sympathetic nervous system and blood pressure change may be constant and independent of the measurement site of the sympathetic activity. In particular, the change in cardiac sympathetic activity is similar to the change in renal sympathetic activity as a function of increasing carotid arterial pressure observed in vagotomized and aortic-denervated rabbits. See Kawada et al, *Differential Dynamic Baroreflex Regulation of Cardiac and Renal Sympathetic Nerve Activities*, American Journal of Physiology—Heart and Circulatory Physiology 2001; Vol. 280; H1581-H1590

Based on these experimental results, the present teachings provide an implantable device and associated methods of monitoring blood pressure indirectly by monitoring changes in sympathetic activity at a selected nerve ending location, such as, for example, at a post-gangliotic neuron location for the kidney. Therapy can also be optionally administered by sympathetic nerve stimulation based on the blood pressure measurement using, for example, stimulation systems and methods disclosed in commonly owned U.S. Pat. No. 6,073, 048, issued Jun. 6, 2000, and in co-owned U.S. Pat. No. 6,745,079, issued Jun. 1, 2004, which are incorporated herein by reference.

Figure 3:
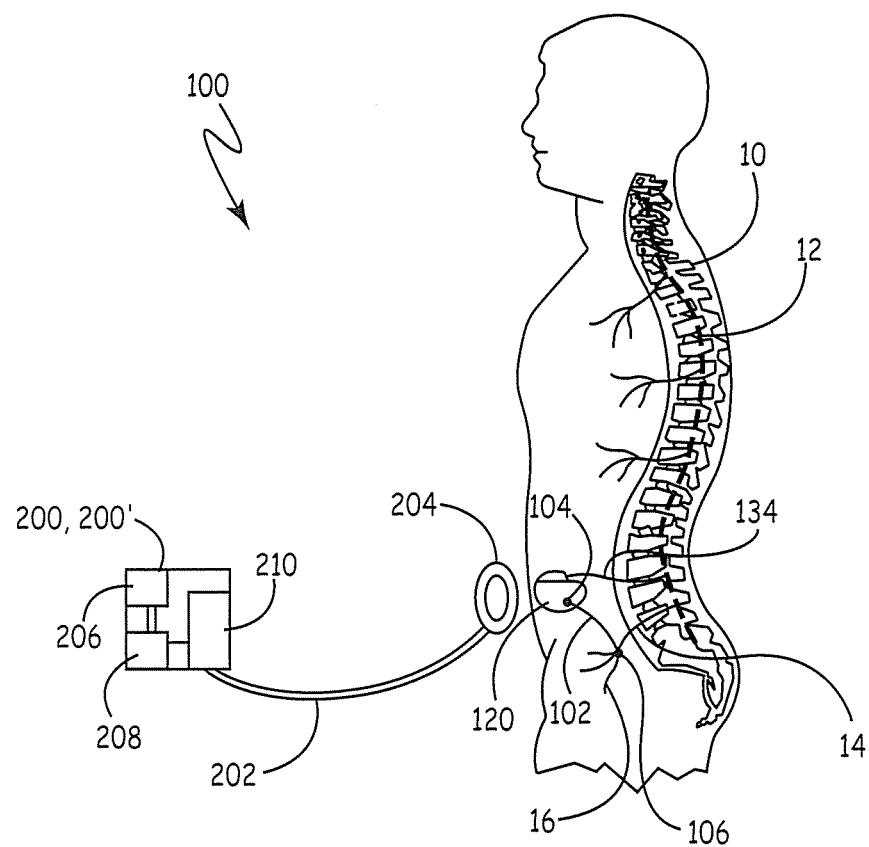
FIG. 3 is a schematic environmental view of an implantable blood pressure monitoring system according to the present teachings.
Figure 4:
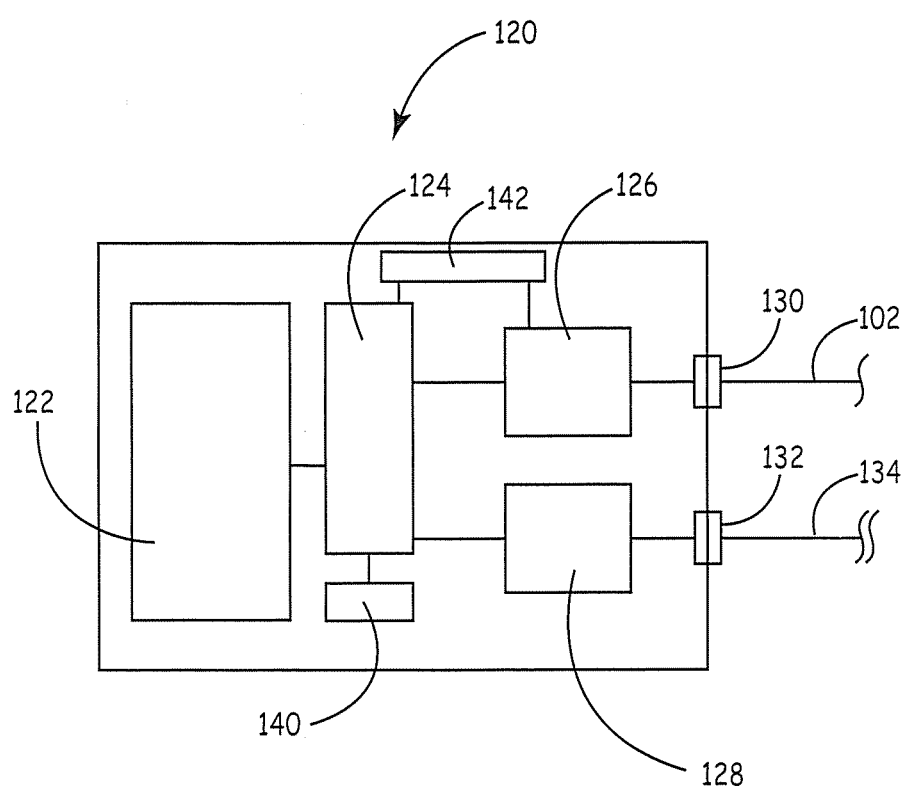
FIG. 4 is a schematic illustration of an implantable blood pressure monitor according to the present teachings.

An exemplary blood pressure monitoring apparatus 100 according to the present teachings is illustrated schematically in FIG. 3. The blood pressure monitoring apparatus 100 can include an implantable device 120 which can be implanted subcutaneously in a patient. The blood pressure monitoring apparatus 100 can include a sending/recording lead 102 for sensing sympathetic nerve activity and, optionally, a therapy lead 134 for delivering sympathetic nerve stimulation. The recording lead 102 and therapy lead 134 are operably coupled to the implantable device 120 at connectors 130, 132 respectively, as shown in FIG. 4. The recording lead 102 can have a first end 104 coupled to the implantable device 120 and a second end 106 positioned adjacent to post-gangliotic nerve endings 16 of the pelvic nerve 14 that extends from the sympathetic trunk 12 along the spine 10 of the patient. The second end 106 of the recording lead 102 can also be wrapped around the trunk of the pelvic nerve 14. The recording lead 102 can be, for example, a cuff electrode of the type disclosed in co-owned U.S. Pat. No. 4,341,221, issued Jul. 27, 1982, the disclosure of which is incorporated herein by reference.

The therapy delivery lead 134 can be, for example, in the form of a pair of bipolar stimulation electrodes or other electrodes, as disclosed in commonly owned U.S. Pat. No. 6,073, 048 issued Jun. 6, 2000, or in commonly owned U.S. Pat. No. 6,745,079 issued Jun. 1, 2004, or in commonly owned U.S. Patent Publication 2007/0156200, the disclosures of each of which are incorporated herein by reference.

The blood pressure monitoring apparatus 100 can also include an external programmer and/or controller and/or monitor 200 ("programmer 200" for short) that can communicate wirelessly with the implantable device 120. The programmer 200 can include, for example, a conductor 202 coupled to a radio-frequency antenna 204 for radio-frequency communication with the implantable device 120 after implantation.

The programmer 200 can be, for example, a wireless telemetry programmer, such as one of the models of the Medtronic CareLink® programmers, which are commercially available from Medtronic, Inc., Minneapolis, Minn. This Medtronic CareLink® programmer uses the Medical Implant Communications (MICS) radio frequency band and is configured to automatically search for the clearest MICS channel available. The programmer 200 can include a power supply 206, data storage 208 and processor circuitry 210, with receiver, transmitter, storage and wireless communication modules. The programmer 200 can be operable to interrogate the implantable device 120, receive data from the implantable device 120, and transmit data to the implantable device 120 and generally program the implantable device 120. An internet-based handheld wireless monitor 200', such as the CareLink® Monitor, commercially available from Medtronic, Inc., Minneapolis, Minn., can be included as part of the blood pressure monitoring apparatus 100 and can be used by the patient to send data to a clinic or physician's office via a standard phone line.

Referring to FIG. 4, the implantable device 120 can include a power supply 122, a processor 124, and a data recording and storage module 126 coupled to the recording lead 102 via the connector 130. The implantable device 120 can also include a neurological pulse generator 128 coupled to the connector 132. The pulse generator 128 can be integral with the implantable device 120, as illustrated in FIG. 3, or a separate implantable component such as, for example, the pulse generator Itrel II® or Synergy®, which are commercially available from Medtronic, Inc., Minneapolis, Minn.

The processor 124 can receive the sympathetic nerve activity transmitted by the recording lead 102, process it to determine whether a threshold value for corresponding changes in blood pressure has been exceeded and provide various outcomes. For example, the processor 124 can instruct a feedback module 140 to deliver direct feedback to the patient in the form, for example, of an audible tone, or a short vibration. The processor 124 can also instruct a communications module 142 to communicate wirelessly with a medical alert system or with a patient's wireless communication device, including a cell phone or a medical monitor 200' for transmitting information automatically to a medical center. The processor 124 can also determine appropriate nerve stimulation therapy based on the calculated nerve activity changes and corresponding blood pressure changes and instruct the pulse generator 128 to provide corresponding nerve stimulation via the therapy lead 134. The therapy mode of the processor 124 and the pulse generator can operate, for example, as described in commonly owned U.S. Pat. No. 6,073,048, U.S. Pat. No. 6,745,049, and U.S. Patent Publication 2007/0156200, referenced above. For example, if the processor 124 determines hypotension based on a comparison of the measured nerve activity changes versus nerve activity change threshold TV corresponding to blood pressure changes or fluctuations with the normal range of the particular patient, the processor 124 can transmit an electrical signal via the therapy lead 134 to stimulate the renal sympathetic nerve activity and lead to an increase in blood pressure. Conversely, if hypertension is detected based on a comparison of the measured nerve activity changes versus nerve activity change threshold TV corresponding to blood pressure changes or fluctuations with the normal range of the particular patient, the processor 124 can transmit an electrical signal via the therapy lead 134 to reduce the renal sympathetic nerve activity and lead to a reduction in blood pressure. The process can be repeated until the patient's blood pressure returns to normal.

Figure 5:
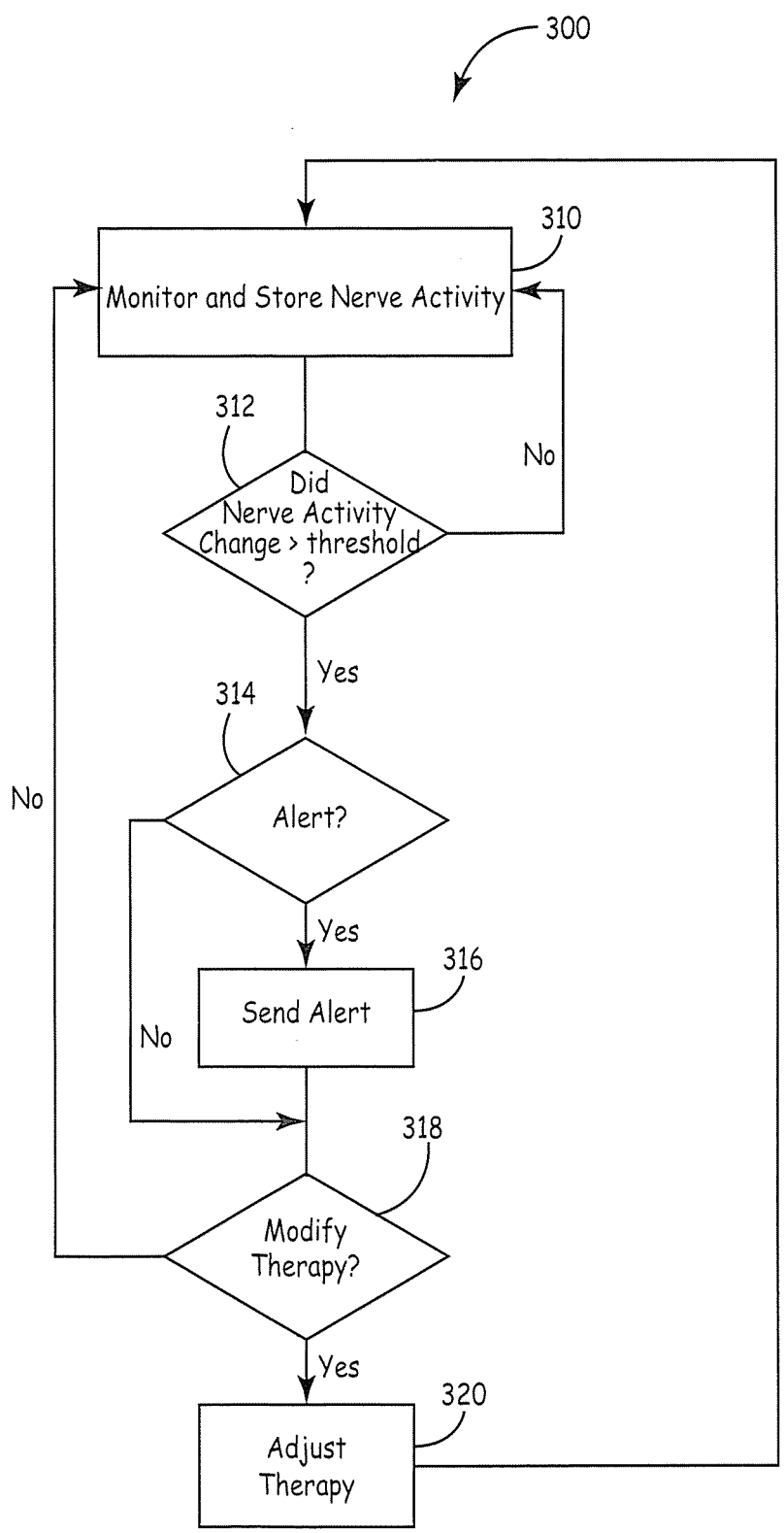
FIG. 5 is a flow chart of a method of monitoring blood pressure according to the present teachings.

Referring to FIG. 5, a method for monitoring blood pressure is illustrated at 300 in a flowchart. As discussed above, the recording lead 102 can collect, transmit and store nerve activity in storage module 126, as shown at block 310. The processor 124 can calculate the nerve activity change, compare with the threshold value TV for the patient and determine whether the change exceeds a threshold value TV at block 312. If the threshold value TV is not exceeded, the monitoring process continues. If the threshold value TV is exceeded, a decision can be made whether or not to send an alert at block 316 depending on the severity of the detected nerve activity changes, the patient's medical characteristics and other known factors.

As discussed above, the alert notification can take various forms. In various exemplary embodiments, the alert can be in the form of an audible tone or other vibration to the patient, and can be customized to the patient. For example, different tones can indicate either high or low blood pressure based on the tone quality or vibration length and can also indicate the severity, using a predetermined number of short alerts corresponding to different severities and associated risks. In response, the patient can take appropriate action, such as stopping current activities that elevate the risk, contacting a medical center, calling emergency help, or initiating transmission of data to a medical center using a wireless monitor 200', as discussed above. In various other exemplary embodiments, an alert can be sent wirelessly through either a wireless link embedded in the communication module 142 of the implantable device 120 and triggered by the processor 124 or by automatically triggering a monitor 200' carried by the patient.

Whether an alert notification option is used or not, a decision whether to initiate or modify therapy can be made at block 318 based on nerve activity information recorded at the storage module 126 and analyzed by the processor 124 for the health parameters and risk factors of the particular patient. For example, a predetermined and stored therapy plan followed by the processor can be modified or adjusted at block 320. Adjustments or modifications can include changes in the amplitude, duration, and frequency of the electrical stimulation signals transmitted by the therapy lead 134 to increase or decrease nerve activity based on the patient's characteristics and current nerve activity accessed and analyzed by the processor 124. After therapy adjustment, monitoring and storing of nerve activity can resume.

In various embodiments, the alert notification can be optional and bypassed in favor of an option to provide treatment as described above. In other embodiments, both the alert notification and treatment can be optional and the implantable device can function passively as a recording device of nerve activity. The patient can periodically transmit the data to a medical center via the monitor 200' or visit a medical center to provide data via the center's programmer 200.

The recording lead 102 and the therapy lead 134 can be implanted by local incision near a selected implantation site for recording sympathetic nerve activity, such as near the kidney nerve or other selected nerve ending site. The implantable device 120 can be inserted subcutaneously using a tunneling tool in a desired location in proximity to and for coupling with the recording lead 102 and the therapy lead 134. Various tunneling tools are commercially available from Medtronic, Inc., Minneapolis, Minn.

The blood pressure monitoring apparatus 100 and associated method of the present teachings provide an implantable device 120 that can monitor and record changes in a patient's nerve activity and correlate such changes with changes in blood pressure, thereby avoiding intravascular or other direct blood pressure measurement. The implantable device can be combined with a therapy module that generates a therapeutic nerve activation pulse for stabilizing blood pressure within a normal range. It should be appreciated that the implantable device 120 can also be combined with other therapeutic modules as appropriate for a particular patient, including, for example, pacemaking or other cardiac synchronization therapies.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A method for monitoring blood pressure comprising:
   implanting a medical device including a processor and a storage module in a patient;
   coupling a first end of a recording lead to the medical device;
   inserting a second end of the recording lead adjacent a sympathetic nerve ending;
   transmitting sympathetic nerve activity via the recording lead to the medical device;
   recording sympathetic nerve activity in the storage module as stored nerve activity data;
   determining changes in sympathetic nerve activity from the stored nerve activity data; and
   determining corresponding changes in blood pressure from the changes in sympathetic nerve activity,
   wherein inserting the second end of the recording lead adjacent a sympathetic nerve ending includes positioning the second end of the recording lead at a post-gangliotic nerve ending for a kidney.

2. The method of claim 1, further comprising:
   comparing changes in sympathetic nerve activity to a threshold value for the patient; and
   providing an alert signal indicative of a blood pressure status.

3. The method of claim 2, wherein providing an alert signal includes providing an alert signal to the patient.

4. The method of claim 2, wherein providing an alert signal includes wirelessly transmitting data to a medical center.

5. The method of claim 1, further comprising:
   comparing changes in sympathetic nerve activity to a threshold value for the patient; and
   providing nerve stimulation therapy via a therapy lead electrically coupled to a pulse generator of the medical device.

6. The method of claim 1, further comprising wirelessly transmitting the stored nerve activity data from the medical device to a medical center via an external handheld medical monitor.

7. The method of claim 1, further comprising wirelessly communicating with the medical device via an external telemetry programmer.

\* \* \* \* \*